United States Patent
Myers

Patent Number: 5,935,100
Date of Patent: Aug. 10, 1999

[54] PRESSURE DIFFERENTIAL VALVE AND INFUSION SET

[76] Inventor: Jan Willem Marinus Myers, Mecklenburgstr. 9, 5913 TP Venlo, Netherlands

[21] Appl. No.: 08/800,779

[22] Filed: Feb. 13, 1997

[30] Foreign Application Priority Data

Feb. 13, 1996 [DE] Germany ............ 196 05 217

[51] Int. Cl.⁶ .......................................... A61M 5/14
[52] U.S. Cl. ...................... 604/81; 604/80; 604/258; 251/61
[58] Field of Search ................ 604/80, 81, 258, 604/142; 251/61, 61.1, 142, 149

[56] References Cited

U.S. PATENT DOCUMENTS

| | | |
|---|---|---|
| 4,237,880 | 12/1980 | Genese . |
| 4,343,305 | 8/1982 | Bron . |
| 4,534,764 | 8/1985 | Mittleman et al. . |
| 4,966,199 | 10/1990 | Ruschke . |
| 5,025,829 | 6/1991 | Edwards et al. . |
| 5,520,661 | 5/1996 | Lal et al. . |

FOREIGN PATENT DOCUMENTS

| | | |
|---|---|---|
| 0 612 537 A2/A3 | 8/1994 | European Pat. Off. . |
| 27 13 618 | 10/1977 | Germany . |
| 27 13 618 C2 | 10/1977 | Germany . |
| 30 35 301 | 4/1981 | Germany . |
| 82 14 927 U | 9/1982 | Germany . |
| 32 15 329 | 12/1982 | Germany . |
| 86 03 917 U | 5/1986 | Germany . |
| 38 03 380 A1 | 8/1989 | Germany . |
| 41 42 494 A1 | 7/1993 | Germany . |
| 42 01 258 | 7/1993 | Germany . |
| 93 19 810 | 3/1994 | Germany . |
| 43 09 262 | 6/1994 | Germany . |
| 43 04 949 A1 | 8/1994 | Germany . |
| 40 39 814 A1 | 6/1995 | Germany . |
| WO 88/02639 | 4/1988 | WIPO . |
| WO 96/03166 | 2/1996 | WIPO . |

*Primary Examiner*—John D. Yasko
*Assistant Examiner*—N. Kent Gring

[57] ABSTRACT

A method and infusion set for consecutively draining liquid medicines from a plurality of containers, such as two containers (1, 2) containing said liquid medicines, the liquid medicine via a differential pressure valve (5a) is fed into a drip chamber (6), wherein the fluid flow is permitted initially from one container (1) by the higher fluid pressure and differential force area from the first container (1) on a diaphragm disk (15), whereby the fluid flow from the second container (2) is stopped and, later an automatic switch to a second container (2) as a source of fluid is effected when the fluid flow from the almost drained first container (1) is at a lower fluid pressure and a smaller differential force area and is exceeded by a higher fluid pressure of the second container (2) and the larger differential force area.

23 Claims, 4 Drawing Sheets

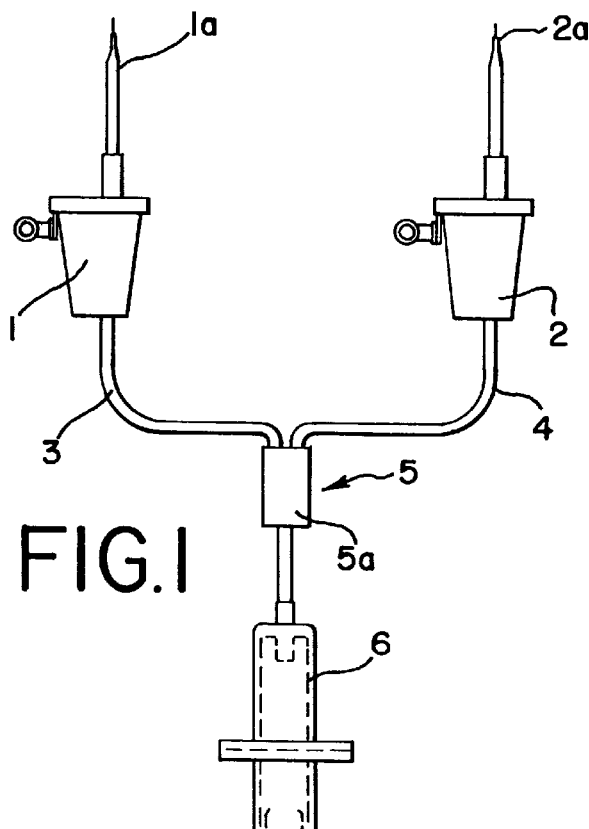
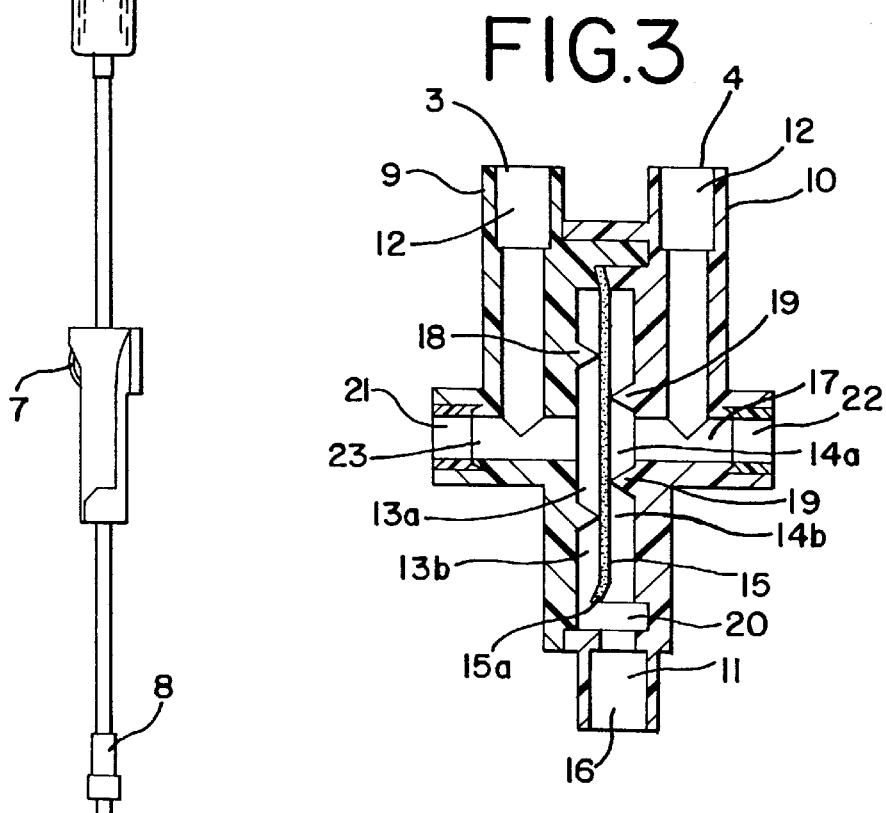

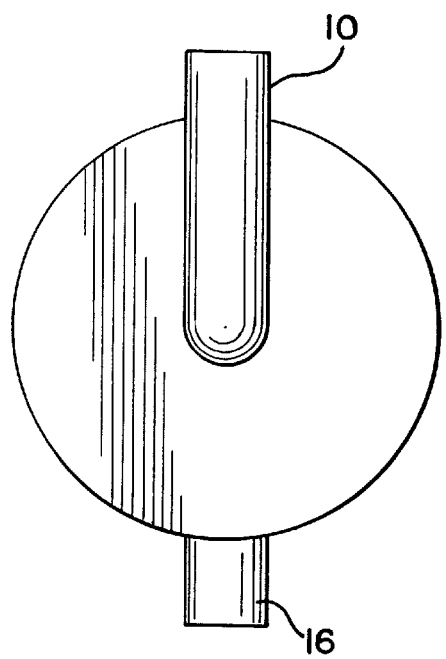
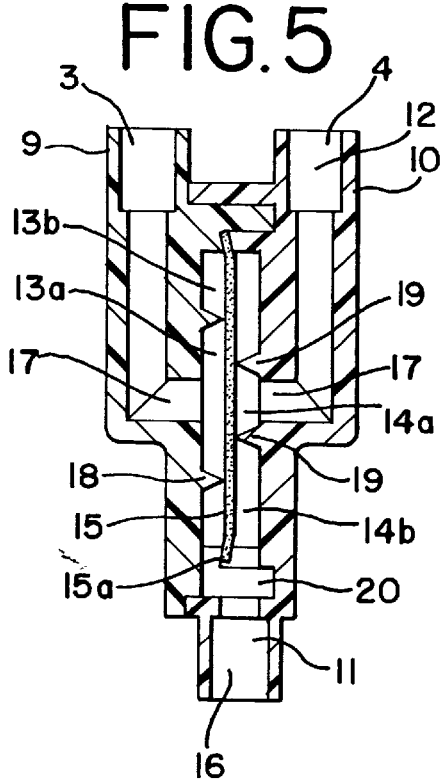
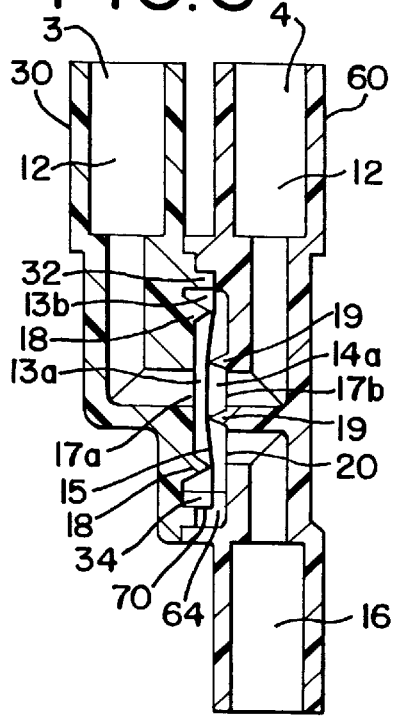
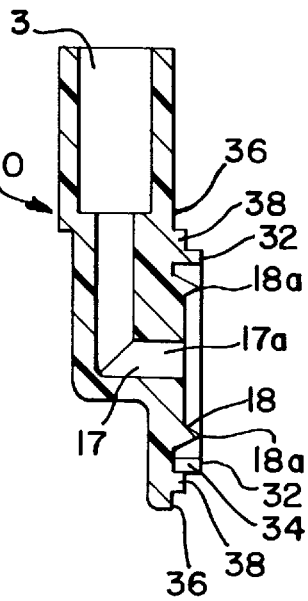
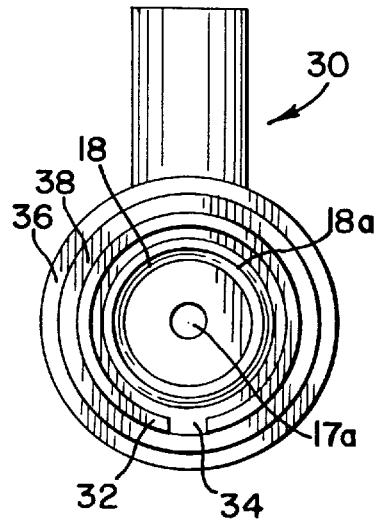

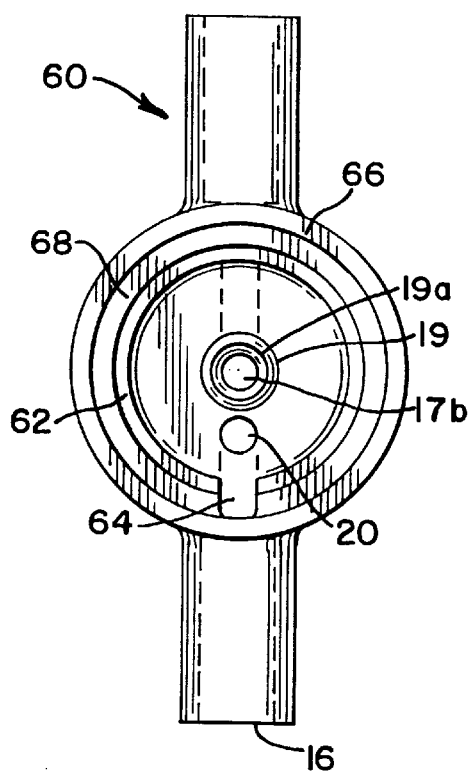
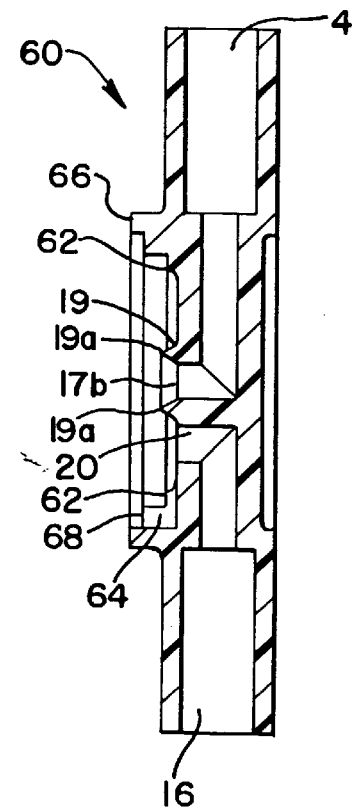
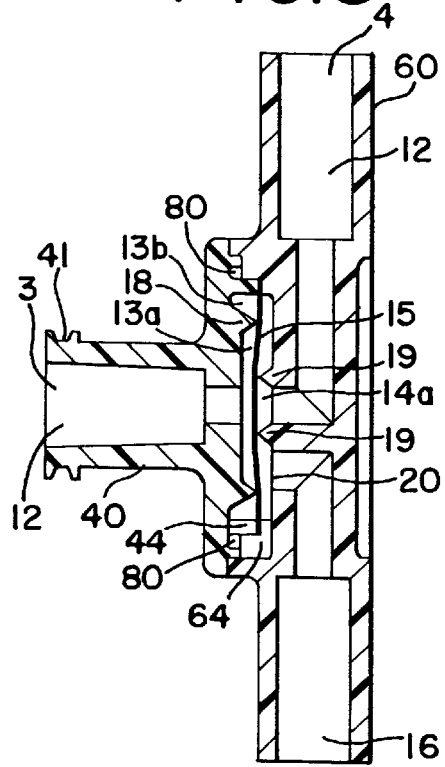
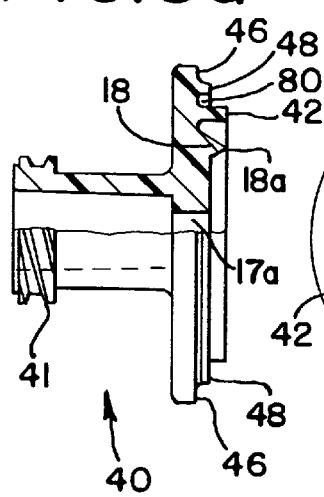
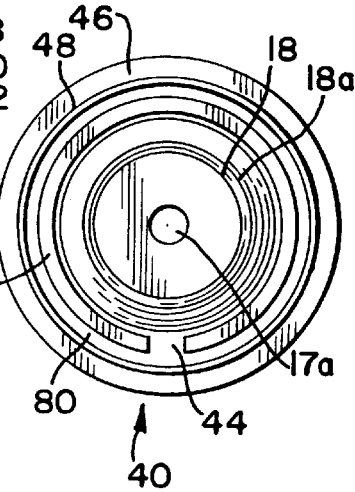

PRESSURE DIFFERENTIAL VALVE AND INFUSION SET

FIELD OF THE INVENTION

The invention relates to a method and an infusion set for consecutively draining or emptying a plurality of containers, especially two containers, filled with liquid medicines within an infusion set in which the liquid medicine is directed by feed lines, a valve and a drip chamber to the front end of the infusion set that may be controlled by a roller clamp.

BACKGROUND OF THE INVENTION

Between the infusion containers and the drip chamber in general there is provided a valve for controlling the amounts. This function in the known valves is supplemented by the construction of the valve as check valves. Such check valves may contain a diaphragm disk (see, for example, DE 40 39 814 A1; DE 43 04 949 A1). Depending on the pressure on the front or rear sides of the diaphragm disk, a flow path is opened or closed permitting fluid to flow from the infusion containers.

In the present case, there exists the problem that after draining one infusion container, a fresh full container must replace the empty container, which usually requires a number of manual steps.

SUMMARY OF THE INVENTION

The present invention provides for an uncomplicated and quick switch over from a first container to a second container if at least two such containers are present. The task of the present invention is to solve the above-noted problem by a method that includes liquid medicine being directed from at least two suspended containers allowing fluid into a drip chamber, via a diaphragm disk differential pressure valve, including the steps of permitting liquid medicine to flow from the first container due to the higher fluid pressure and due to a larger differential force area on the diaphragm disk, while the flow from the second container is stopped, and automatically switching from the first container to the second container in response to the first container being at a lower fluid pressure and a smaller differential force area on the diaphragm disk and thereby permitting liquid medicine to flow from the second container. In addition to other advantages noted herein, the automatic switch over method herein allows for a draining or emptying of the first container without admitting air bubbles.

Further, the present invention includes an infusion set with containers for liquid medicines, each connected by feed lines to a differential pressure valve, in turn connected to a drip chamber, and in turn further connected by a feed line leading to the front end that is controlled by a roller clamp. The switch over element for automatically opening a full container after a container is drained, according to the present invention, comprises a differential pressure valve into which a plurality of feed lines from respective liquid medicine containers each lead into respective differential force chambers provided therein, a portion of each differential force chamber sealably separated from a portion of the other differential force chamber by means of a diaphragm disk, and wherein each differential force chamber drains to a drain line for the liquid medicine.

One embodiment of the invention is provided with a valve having two valve housing halves that are sealed together, one valve housing half having one drain line entry, and each valve housing half having one feed line entry. This design provides two differential force chambers and thereby permits the combination of two fluid flows from different differential force chambers. This embodiment further includes in each differential force chamber of each valve housing half an annular ridge or lip-shaped sealing ring concentric to a fluid channel provided in each housing half, wherein a first annular ridge or sealing ring associated with the housing half that is in fluid communication with the first liquid medicine container has a larger diameter than the annular ridge or sealing ring associated with the housing half that is in fluid communication with the second liquid medicine container. By this construction, only one diaphragm disk is necessary and is adapted to engage annular ridges or sealing rings and is uniformly tensioned at the circumference of both valve housing halves when sealed together, which therefore safely performs the important function of sealing the diaphragm disk against the annular ridges or sealing rings at suitable pressure differentials.

The desired sealing at very small pressures is obtained by an embodiment with a circular diaphragm disk produced from a sheet of liquid silicone, silicone rubber, or natural rubber, or a mat of liquid silicone, silicone rubber, or natural rubber. A further feature of an embodiment is that the diaphragm disk circumference contacts the valve housing halves and is positioned at an opening leading into the drain line, and thus a common drain line is formed for two fluid flows. Another feature of an embodiment is that fluid channels communicating with respective pressure differential chambers open coaxially to the respective annular ridges or sealing rings provided within the respective chambers. A further feature of an embodiment includes a drain line that drains from the side of one differential chamber, the drain entry being within the diameter of the sealing ring of the other differential chamber.

In an alternative embodiment, the fluid channels communicating with respective chambers are at an angle, and air relief lines may be connected to the angular fluid channels, wherein the air relief lines contain hydrophobic filter diaphragms. In this embodiment, it is thus advantageously possible to vent the pressure differential chamber entry feed lines, the differential force chambers, and the drain line.

In another alternative embodiment, the valve is provided with a primary housing that includes an inlet that provides a first liquid source, about which a sealing ring projects and adjacent the sealing ring is a drain outlet, and a secondary housing that includes an inlet that provides a second liquid source, about which a sealing ring projects having a diameter greater than the diameter of the first inlet sealing ring, and a diaphragm disk clamped between the primary and secondary housings overlying and sealingly engaging the sealing rings, with portions of the housings defining a bypass channel permitting fluid communication between the secondary housing sealing ring and the drain outlet. A further feature of an embodiment includes a threaded connection for the secondary housing and/or a rubber or otherwise medically approved substance serving as an injection site that allows for the introduction of medications into the second liquid source via a hypodermic needle or the like when desired.

Other features and advantages of the present invention will become more fully apparent from the following description of the embodiments and their features, the accompanying drawings, and the appended claims.

BRIEF DESCRIPTION OF THE DRAWINGS

FIG. 1 is a general side view of an embodiment of the assembled components for an infusion set.

FIG. 2 is a side view of an embodiment of a differential pressure valve with air relief lines.

FIG. 3 is a central axial cross-section of the differential pressure valve of FIG. 2.

FIG. 4 is a side view of an alternative embodiment of a differential pressure valve without air relief lines.

FIG. 5 is a central axial cross-section of the differential pressure valve of FIG. 4.

FIG. 6 is a central axial cross-section of another embodiment of a differential pressure valve that has a side view similar to that of FIG. 4.

FIG. 6a is a central axial cross-section of a component of the differential pressure valve of FIG. 6.

FIG. 6b is a plan view of the differential pressure valve component of FIG. 6a.

FIG. 7a is a central axial cross-section of a second component of the differential pressure valve of FIG. 6.

FIG. 7b is a plan view of the differential pressure valve component of FIG. 7a.

FIG. 8 is a central axial cross-section of another embodiment of the differential pressure valve that has a different first component than FIG. 6.

FIG. 8a is partially broken-out central axial cross-section of a first component of the differential pressure valve of FIG. 8.

FIG. 8b is a plan view of the differential pressure valve component of FIG. 8a.

FIG. 9b is a plan view of the differential pressure valve component of FIG. 9a.

DETAILED DESCRIPTION OF THE DRAWINGS AND THE PRESENTLY PREFERRED EMBODIMENTS

Figure 9:
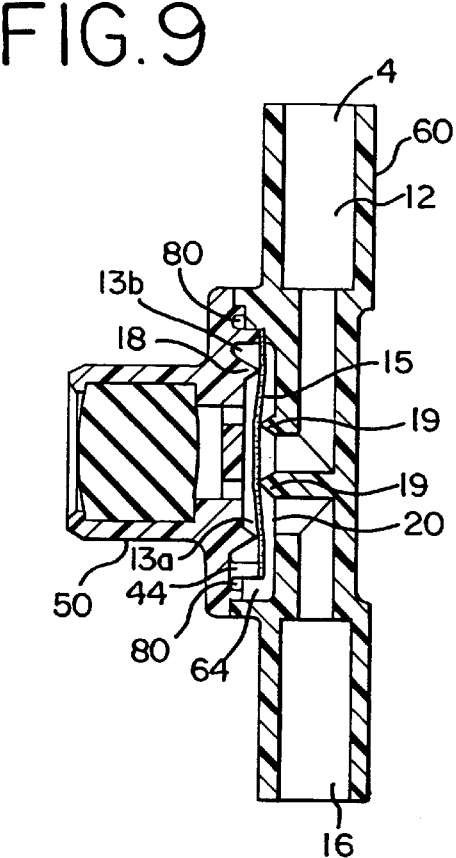
FIG. 9 is a central axial cross-section of yet another embodiment of the differential pressure valve that has another first component than FIG. 6.

As shown in FIG. 1, a first container 1 is used for a chosen liquid medicine which can be different from the liquid medicine in a second container 2 or which can be the same. The liquid medicine is introduced by piercing means such as spikes 1a or 2a, respectively, that are for example from an ampulla. The first container 1 is connected to a first feed line 3 and the second container 2 is connected to a feed line 4 and both feed lines are connected to a valve 5 consisting of a differential pressure valve 5a more detailedly described below. The fluid medicine communicates with a drip chamber 6 via valve 5 and associated line and is under the control of a roller clamp 7 that in turn is fed to the front end 8 of the infusion set from where as usual it is introduced into the body of a patient.

One embodiment of a pressure differential valve of the present invention is shown in FIGS. 2–3 and another embodiment, with similar features denoted by identical numerals, is shown in FIGS. 4–5. The liquid medicine is directed via the differential pressure valve 5 from the suspended containers 1 or 2 into the drip chamber 6. A feed line 3 of the first container 1 and a feed line 4 of the second container 2 leads to the differential pressure valve 5. Both feed lines 3 and 4 open into respective differential force chambers 13 and 14 which are sealingly separated from each other by the diaphragm disk 15. Both differential force chambers 13 and 14 are connected to a drain line 16 for the liquid medicine.

With reference to FIGS. 2–5, the differential pressure valve comprises two valve housing halves 9 and 10 which are adapted to sealingly contact each other, and after the mounting of the diaphragm disk 15 therein, the valve housing halves 9 and 10 are sealed together thereby clamping securely diaphragm disk 15 therebetween. One of the valve housing halves, either half 9 or half 10, includes a drain line entry 11 for connection to an appropriate drain line 16, and each valve housing half 9 and 10 also includes a feed line entry 12. Valve housing halves 9 and 10 when assembled together with diaphragm disk 15 provide differential force chambers 13 and 14, respectively, within the valve. Annular ridge 18 of housing half 9 may, depending upon operating conditions as discussed below, establish a seal with diaphragm disk 15 that demarcates differential force chamber 13 into a circular chamber 13a and annular chamber 13b. Similarly, annular ridge 19 of housing half 10 may, again depending upon the operating conditions more fully explained below, establish a seal with diaphragm disk 15 that demarcates differential force chamber 14 into a circular chamber 14a and annular chamber 14b. Accordingly, the respective annular ridges 18, 19 may also be termed lip-shaped sealing rings 18, 19. Annular ridge 18 has a larger diameter than annular ridge 19.

Diaphragm disk 15 includes a perimeter portion 15a positioned at opening 20 that leads to the drain line 16. In this embodiment, diaphragm disk 15 is circular and produced from a sheet of liquid silicone, silicone rubber, or natural rubber or from a mat of liquid silicone, silicone rubber or natural rubber, and thus portion 15a is a part of the circumference of diaphragm disk 15. Further, opening 20 is in direct fluid communication with annular chamber 13b and annular chamber 14b irrespective of whether diaphragm disk 15 is sealed against annular ridges 18, 19. Also, in direct fluid communication with circular chambers 13a, 14a are fluid channels 17. In this embodiment, fluid channels 17 open coaxially to the respective circular chambers 13a, 14a and annular ridges 18, 19, and provide a fluid path that is at an angled shape, such as a 90° elbow.

In an alternative embodiment shown in FIG. 3, air relief lines 21 and 22, respectively, are connected to the fluid channels 17, wherein alternatively such air relief lines can be dispensed with in view of other well-known steps for air relief (see FIG. 5). In each of the air relief lines 21 and 22, respectively, there is inserted a hydrophobic filter diaphragm 23 which, on the one hand, is air-permeable but, on the other hand, is not permeable for liquids. The hydrophobic filter diaphragm may be a hydrophobic membrane ranging from 0.02 to 0.8 micron pore size.

The diaphragm disk 15 is preferably circular and stamped or die cut from a sheet or band of liquid silicone, silicone rubber, or natural rubber. The thickness of the diaphragm is preferably uniform and may vary, dependent on the desired pressure differential between chambers, from 0.2 to 0.5 mm. The thickness tolerance varies by the manufacturing method of the sheet or mat of the diaphragm material. The preferred embodiment consists of silicone rubber and has a diameter of about 13.5 mm, a thickness of about 0.3 mm, and a hardness of 40 degrees Shore A.

Further, the annular ridges 18, 19 or lip shaped sealing rings, are preferably about 60° in cross-section and each ridge is integral with the respective housing half. The ratio of the diametric apex for the sealing ridge of ring 18 to the diametric apex for the sealing ridge or ring 19 is preferably chosen to be a ratio of about three to one. In this preferred embodiment, it is thus believed that the hydrostatic pressure on the side of the diaphragm disk with the larger diametric apex for the sealing ridge must be less than one-third of the hydrostatic pressure of the fluid source associated with the sealing ridge with the smaller diametric apex before the diaphragm moves to open the side that engages the sealing ridge with the smaller diametric apex, and thus permit liquid to be transported to the patient from another fluid source associated with the smaller diametric apex sealing ridge.

Operation of the embodiments of the pressure differential valve is as follows. The fluid flow starts from the first container because of the higher fluid pressure and a larger differential force area of the first container 1 fluid via circular chamber 13*a* in front of the diaphragm disk 15 (see e.g., FIGS. 3 and 5) while the liquid flow from the second container 2 remains stopped because the larger differential force area prevents the flow of the liquid medicine from the second container 2. As soon as the liquid level of the first container and associated feed line decreases to a point where they are almost empty, the liquid pressure decreases such that the larger differential pressure area on the side of the diaphragm disk 15 corresponding to circular chamber 13*a* falls below the opening force created by the high fluid column of the second container 2 fluid via circular chamber 14*a*, whereby automatically liquid medicine flow is switched over from the first container 1 to the second container 2.

Accordingly, the use of the above-described infusion set embodiment may occur for example when using consecutively two infusion solutions to be administered to a patient. Under such use conditions, and during the liquid flow from the first container 1, the liquid flow may suck air from the area of the second container 2, which possibly has to be vented. Thereafter the roller clamp 17 may be adjusted to the desired dripping rate, and the first container is emptied whereafter the switch over to the second container occurs automatically. At the time of the automatic switch over and thereafter during the fluid flow operation, there is an overpressure of the fluid flow from the second container 2, and the diaphragm disk 15 is pressed onto the annular ridge 18 and also is lifted from the annular ridge 19 such that the liquid medicine can drain from the second container 2 to the patient.

An alternative embodiment is shown in FIGS. 6–7*b*, in which like reference numerals indicate like parts and features as the above figures. Primary housing half 60 and secondary housing half 30 are sealingly engaged. Like the other embodiments, one housing half includes annular ridge 18 provided with a sealing lip apex 18*a* and the other housing half is provided with annular ridge 19 that includes sealing lip apex 19*a*. Secondary housing 30 (see FIGS. 6*a–6b*) is provided with inlet 17*a*, about which is located annular ridge 18. Secondary housing 30 includes a compression ring 32 that projects from the secondary housing 30 body and has a diameter greater than annular ridge 18. Compression ring 32 is provided with compression ring passage 34, that in conjunction with valve space passage 64 (discussed below) allows for fluid communication between annular chambers 13*b* and 14*b* in the assembly of the housing halves 30, 60. Secondary housing 30 is further provided with first sealing ring projection 36 that has a diameter greater than that of the compression ring 32 and allows for sealing engagement of the housing halves. Secondary housing 30 may also have a secondary sealing ring 38 that may provide an alternative sealing engagement member for the assembly.

Primary housing half 60 (see FIGS. 7*a–7b*) is provided with inlet 17*b* about which is located annular ridge 19, that in turn includes sealing lip apex 19*a*. Outside of annular ridge 19 is located opening 20 that is in fluid communication with drain line 16 (see FIGS. 7*a–7b*). Encircling annular ridge 19 and opening 20 is ring shaped seat 62 that is discontinuous and provided with a valve space passage 64. Ring shaped seat 62 is adapted to clamp diaphragm disk 15 between ring shaped seat 62 and compression ring 32 when the housing halves are assembled (see FIG. 6). Encircling ring shaped seat 62 is sealing ring projection 66 which is continuous and adapted to engage first sealing ring projection 36 of the secondary housing when the housing halves are assembled. Intermediate sealing ring projection 66 and ring shaped seat 62 is secondary sealing ring 68 that is of sufficient height to allow for the fluid communication between compression ring passage 34 and valve space passage 64 when the housing halves are assembled. The aforementioned combination of the valve space passage 64 overlying compression ring passage 34 provides a bypass channel 70 in the assembled housing halves (see FIG. 6). This bypass channel 70 is generally radial in configuration in this embodiment, and the overlying radial passages 34 and 64 are assured in the assembly by way of orienting the respective feed line entry 12 passage in a parallel condition.

In the assembly of the housing halves, the housing halves are sealed together at the interface between the first sealing ring projection 36 and sealing ring projection 66, which in turn clamps the diaphragm 15 between ring shaped seat 62 and compression ring 32. Such joinder may be executed by means of ultrasonic welding or use of medically approved adhesives (e.g., ultraviolet curing adhesives), or a combination thereof. The presently preferred sealing means employs ultrasonic welding. The clamped interface between the disk 15, ring shaped seat 62 and compression ring 32 may also be executed by means of ultrasonic welding or use of medically approved adhesives.

An alternative secondary housing half 40 is shown in FIGS. 8*a–8b*, that in turn may be assembled with primary housing half 60. This assembly is shown in FIG. 8. Referring now in more detail to these drawings, in which like reference numerals indicate like parts and features throughout the several of the above-discussed views, secondary housing 40 (see FIGS. 8*a–8b*) is generally provided with a threaded connection 41 for connecting the housing half 40 to an appropriate liquid medicine feedline. With this design, there is thus the possibility to connect the housing half by means of a male luerlock connection or other medically accepted threaded connection.

Figure 10:
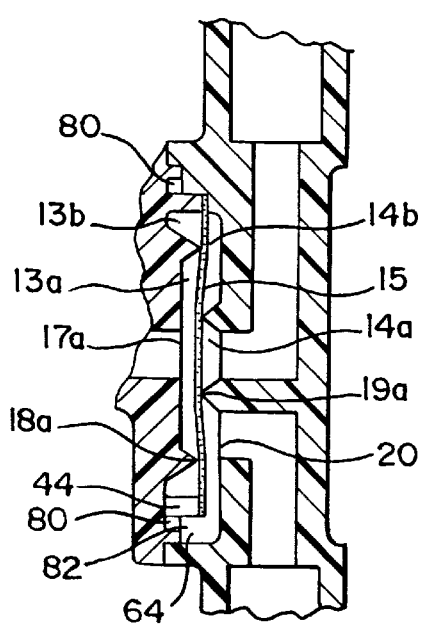
FIG. 10 is a magnified partially broken out central axial cross-section of the embodiments of the differential pressure valve of FIGS. 8–9c.

Further, alternative secondary housing 40 includes a compression ring 42 that projects from the housing 40 that is a diameter greater than annular ridge 18. Secondary housing 40 is further provided with sealing ring projection 46, of a diameter greater than compression ring 42 that permits sealing engagement between housing halves, and secondary sealing ring 48 may provide an alternative sealing engagement for the assembly. Compression ring passage 44, in this embodiment, is generally radial and allows for fluid communication between the annular chamber 13*b* and annular channel 80 provided in secondary housing 40. Thus, in this embodiment of the secondary housing, when assembled with primary housing 60, fluid communication between secondary housing inlet 17*a* and outlet opening 20 is permitted at an appropriate pressure differential between chambers 13 and 14 via fluid passage over sealing lip 18a, and through annular chamber 13b, compression ring passage 44, annular channel 80, valve space passage 64 and annular chamber 14b (see FIG. 10). Of note for this embodiment is that a bypass channel generally denoted 82 formed by the assembly does not require that passages 64, 44 overlie one another due to the provision of annular channel 80. Accordingly, annular channel 80 permits greater tolerances in angular orientation of secondary housing 40 with respect to primary housing 60, and thus this design may be more suitable for automatic assembly. For this reason, among others, bypass channel 82, including annular channel 80, may be preferably utilized in the above-described secondary housing 30, as well as 40, and 50 to which discussion is now directed.

Figure 9A:
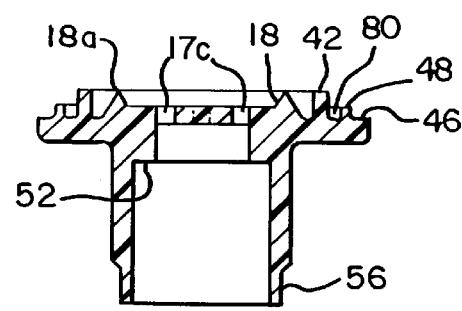
FIG. 9a is a central axial cross-section of a first component of the differential pressure valve of FIG. 9 before insertion of the injection site.
Figure 9B:
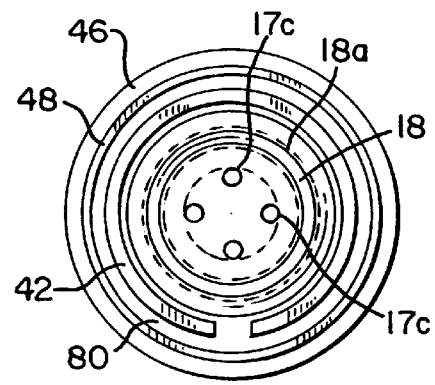
Figure 9C:
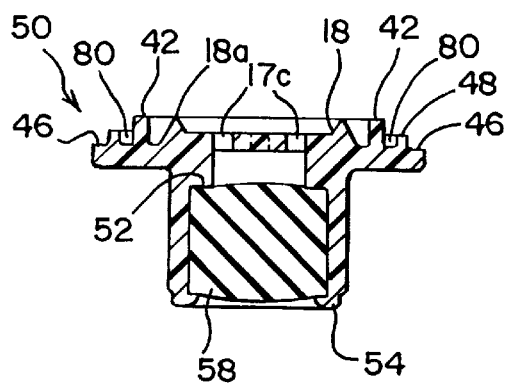
FIG. 9c is a central axial cross-section of the differential pressure valve component of FIG. 9.

Another alternative embodiment of a differential pressure valve is shown in FIGS. 9–9c. Referring now in more detail to these drawings, in which like reference numerals indicate like parts and features throughout the several above-discussed views, there is provided an assembly that is a differential pressure valve that incorporates an alternative secondary housing 50. Alternative secondary housing 50 is provided with a plurality of inlet passages 17c that are in fluid communication with injection site 58. In the preferred embodiment, the injection site 58 is secured by annular shoulder 52 and annular rim 54. In its preferred embodiment, injection site 58 consists of natural rubber of 60° Shore A hardness which is secured in alternative secondary housing 50 by friction rolling or ultrasonics. Rim 54 is formed by either such means due to the raised temperature in combination with the axial compression inherent with these means (see FIG. 9a). In other respects, alternative secondary housing 50 is constructed and assembled like the embodiments immediately described above (see FIG. 10). As can be readily appreciated, the alternative embodiment of the differential pressure valve permits the injection of one or more liquids via a hypodermic needle or the like introduced through the injection site 58. By way of the appropriate pressure differential from the hypodermic needle fluid, liquid medicine from the needle or the like may be introduced into the fluid flow.

In the preferred embodiments of the differential pressure valves, the valve housings may be manufactured of polymeric materials that are generally medically accepted, e.g. polystyrenes, styrenic copolymers (A.B.S.) or polycarbonates. In particular, the preferred material is a styrenic copolymer (A.B.S.) manufactured by BASF Corporation, and sold under the trademark name of Terlux KR2802.

The preferred embodiment for the differential pressure valve differential force chambers 13, 14, including circular chambers 13a, 14a and annular chambers 13b, 14b, are as follows. With respect to the primary housing 60 (FIGS. 7a–7b), housing inlet 17b is about 2.0 mm and opening 20 for drainline 16 has a diameter of about 2.0 mm. Sealing lip apex 19a which engages diaphragm disk 15 when the differential pressure in circular chamber in 14a is insufficient, has a diameter of about 3.0 mm. In radial dimensions (see FIG. 7b), ring shaped seat 62 has a beginning diameter of about 12.0 mm and terminates at a diameter of about 13.6 mm, at which point it rises axially to the secondary sealing ring 68 and this surface extends to a diameter of about 16.0 mm. At the termination of secondary sealing ring 68, sealing ring projection 66 axially rises and continues from about 16.0 to a diameter of about 18.0 mm. In axial cross-sectional dimensions, and with reference to a datum from the sealing ring projection 66 plane (i.e., the left most edge of the housing half depicted in FIG. 7a), the secondary sealing ring 68 plane is about 0.68 mm from the sealing ring projection 66. Further, and with respect to this datum, ring shaped seat 62 is about 1.84 mm from the sealing ring projection 66, and further, the member that forms the annular chamber 14b is about 2.40 mm from this datum. Annular ridge 19 in cross-section is about 60° and sealing lip apex 19a is located about 1.54 mm from the datum of the sealing ring projection 66 plane.

The preferred secondary housing half is configured as follows, with particular reference to the features forming circular chamber 13a and annular chamber 13b of the pressure differential valve (see FIGS. 6a, 6b, 8a, 8b, 9a–9c, 10). Inlet 17a is about 2.0 mm in diameter, and sealing lip apex 18a has a diameter of about 9.0 mm. Compression ring 32 has an inner diameter of about 12.0 mm and an outer diameter of about 13.6 mm. Secondary sealing ring 38 has an outside diameter of about 16.0 mm and inside diameter of about 15.0 mm, and first sealing ring projection 36 has an outside diameter of about 18.0 mm. In axial dimensions, and with reference to the datum of the leading edge of compression ring 32 (the rightmost edge as viewed in FIGS. 6a, 8a and the uppermost edge as viewed in FIGS. 9a, 9c), the sealing lip apex 18a is at about the same plane as compression ring 32 plane, and apex 18a has an angular cross-section of about 60°. The plane of the secondary sealing ring 38 is about 0.86 mm from the datum of the compression ring 32, as is the floor of the circular chamber 13a. The plane of the first sealing ring projection 36 is about 1.54 mm from the datum of the plane of the compression ring 32, as is the plane of annular passage 80. Further, the compression ring passage 34 and valve space passage 64 may overlie one another and are of about 2.0 mm in width (see FIGS. 6b, 8b, 9b). As noted above, however, for configurations that include annular channel 80, passages 34, 64 need not overlie each other.

It is of note that the above-described pressure differential valve has numerous advantages. The disclosed valve is of simple construction, yet provides a reliable valve for operating pressures to which it is suited. It is believed that with the construction of this pressure differential valve as disclosed, the tension in the diaphragm disk can be accurately predetermined and provide automatic switching between fluid sources at predetermined hydrostatic pressures. In this manner, the present invention avoids complicated designs and yet may result in reliably achieving the above-noted pressure differential valve functionality. Further, the design of the above-described embodiments avoids complicated assembly methods by way of limiting the number of highly toleranced dimensions or assembly methods and the like and thus they lend themselves to assemblage by automated equipment.

While the above embodiments of the inventions have been disclosed, they are not limited to the disclosed examples. Modifications discussed above, as well as in addition to those discussed, can be made without departing from the inventions. The scope of the invention is indicated in the appended claims, and all changes that come within the meaning and range of equivalency of the claims are therefore intended to be embraced therein. Thus, while the inventions have been described with reference to particular embodiments, modification of structure, material and the like will be apparent to those skilled in the art, yet still fall within the scope of the invention.

I claim:

1. A method for consecutively draining liquid medicines from a plurality of containers within an infusion set in which the liquid medicine flows through feed lines, a valve and a drip chamber under the control of a roller clamp to the front end of the infusion set, characterized in that the liquid medicine from suspended containers is fed into the drip chamber via a differential pressure valve with a diaphragm disk having a differential force area on one side of the disk in fluid communication with the first container and a larger differential force area on the other side of the disk in fluid communication with the second container, including the steps of permitting liquid medicine to flow from the second container due to the fluid pressure on the larger differential force area on the diaphragm disk while the fluid flow from the first container is stopped, and automatically switching to permit fluid flow from the first container while the fluid flow from the second container is stopped in response to the lowered fluid pressure on the larger differential force area on the diaphragm disk.

2. An infusion set having an outlet front end and containers for liquid medicines, at least a first and second container connected by feed lines (3, 4) to a valve, said valve fluidly communicating with a drip chamber and a drain line leading to the infusion set front end, characterized in that the valve (5) comprises a differential pressure valve (5a) having a first inlet (17b) in fluid communication with the first container (3) and a second inlet (17a) located in opposing relationship to the first inlet (17b) and in fluid communication with the second container (4), a first sealing ring (19) about the first inlet (17b) and a second sealing ring (18) about the second inlet (17a) and of greater diameter than the first sealing ring (19), a compression ring (32) of greater diameter than the second sealing ring (18) that defines a compression ring passage (34, 44), and an imperforate diaphragm disk (15) clamped within the valve by the compression ring (34) and positioned between the first and second sealing rings (18, 19) to thereby provide respective first and second differential force chambers (14a, 13a) defined by the first and second sealing rings (18, 19), separated by the diaphragm disk (15), whereby the respective first and second liquid medicine containers (1, 2) each are in fluid communication with a respective differential force chamber (14a, 13a), wherein each differential force chamber is sealably separated from each other by the diaphragm disk (15) and wherein the second differential force chamber (13a) first fluidly communicates with the drain line (16) due to the larger differential force area on the diaphragm disk (15) from the second differential force chamber, and then following discharge of fluid from the second liquid medicine container (2), the fluid flow from the second differential force chamber (13a) is stopped, and the first differential force chamber (14a) automatically fluidly communicates with the line drain line (16) to permit fluid flow from the first differential force chamber (14a) due to the fluid pressure on the disk from the second differential force chamber (14a).

3. The infusion set according to claim 2, further characterized in that the valve (5) is formed by respective first and second valve housing halves (10, 9) sealed together with the diaphragm disk (15) therebetween, wherein each valve housing half (9, 10) includes a feed line entry port (12).

4. The infusion set according to claim 3, further characterized in that the first housing half (10) includes a compression ring seat (62) defining a valve space passage (64), and the second housing half (9) includes the compression ring (34), the compression ring seat (62) opposing the compression ring (32) and clamping the disk (15) therebetween, and the valve further defining an annular channel (80) around the circumference of the diaphragm disk (15) in fluid communication with the compression ring passage (34, 44) and the valve space passage (64) to thereby provide a bypass channel (82) fluidly communicating the second sealing ring (18) with the drain line (16).

5. The infusion set according to claim 4, further characterized in that each valve housing half is provided with a liquid entry channel (17) having an angular shape and fluidly connecting a feed line port (12) with a differential force chamber (13, 14), and each opening concentrically with a respective annular ridge (18, 19).

6. The infusion set according to claim 4, further characterized in that each angularly shaped fluid channel (17) is connected to a respective air relief line (21, 22) and a hydrophobic filter diaphragm (23) inserted therebetween.

7. The infusion set according to claim 3, further characterized in that the diaphragm disk (15) is generally circular with a part of the circumference (15a) thereof in direct fluid communication with the drain line (16).

8. The infusion set according to claim 3, further characterized in that each valve housing half is provided with a liquid entry channel (17) having an angular shape and fluidly connecting a feed line entry port (12) with a differential force chamber (13, 14) and opening concentrically with each other.

9. The infusion set according to claim 3, further characterized in that each angularly shaped fluid channel (17) is connected to a respective air relief line (21, 22) and a hydrophobic filter diaphragm (23) inserted therebetween.

10. The infusion set according to claim 2, further characterized in that the valve (5) is provided with a compression ring seat (62) defining a valve space passage (64), the compression ring seat (62) opposing the compression ring (32) and clamping the disk (15) therebetween, and the valve further defining an annular channel (80) around the circumference of the diaphragm disk (15) in fluid communication with the compression ring passage (34, 44) and the valve space passage (64).

11. The infusion set according to claim 10, further characterized in that the diaphragm disk (15) is generally circular with a part of the circumference (15a) thereof in direct fluid communication with the drain line (16).

12. The infusion set according to claim 10, further characterized in that the valve (5) is provided with a plurality of liquid entry channels (17) each having an angular shape and leading from a respective feed line (3, 4) to a respective differential force chamber and opening concentrically with each other.

13. The infusion set according to claim 10, further characterized in that each angularly shaped fluid channel (17) is connected to a respective air relief line (21, 22) and a hydrophobic filter diaphragm (23) inserted therebetween.

14. The infusion set according to claim 2, further characterized in that the diaphragm disk (15) includes a portion in direct fluid communication with the drain line (16).

15. The infusion set according to claim 14, further characterized in that each angularly shaped fluid channel (17) is connected to a respective air relief line (21, 22) and a hydrophobic filter diaphragm (23) inserted therebetween.

16. The infusion set according to claim 2, further characterized in that the valve (5) is provided with a plurality of liquid entry channels (17), each having an angular shape and leading from a respective feed line (3, 4) to a respective differential force chamber (13, 14).

17. The infusion set according to claim 2, further characterized in that each angularly shaped fluid channel (17) is connected to a respective air relief line (21, 22) and a hydrophobic filter diaphragm (23) inserted therebetween.

18. The infusion set as in any one of the claims 2 to 17, further characterized in that the diaphragm disk (15) is produced from a sheet or mat of material selected from the group consisting of liquid silicone, silicone rubber or natural rubber.

19. A pressure differential valve for use in infusion sets provided with at least a first and second fluid source and a drain comprising:

a primary housing half having an inlet and outlet passage for fluid from a first fluid source, a lip-shaped sealing ring about the outlet passage, a discontinuous ring shaped seat about the sealing ring, thereby defining a valve space passage, and a continuous first ring projection about the discontinuous ring shaped seat, said housing further provided with a drain passage located between the lip shaped sealing ring and the discontinuous ring shaped seat;

a secondary housing half having an inlet and outlet passage for fluid from a second fluid source, a lip shaped sealing ring about the secondary housing outlet, a discontinuous compression ring about the secondary housing sealing ring, thereby defining a compression ring passage, and a continuous second ring projection about the compression ring adapted to overlie the first ring projection of the primary housing half, an imperforate flexible diaphragm overlying the primary and secondary housing half sealing rings and disposed between the ring-shaped seat and compression ring;

means for sealing the primary housing half first outer ring projection with the secondary housing half second outer ring projection, thereby clamping the diaphragm between the ring-shaped seat and compression ring to allow the lip shaped rings of the primary and secondary housings to sealingly engage the diaphragm; and bypass channel means, including the valve space passage and compression ring passage, for fluid communication between the secondary housing half sealing ring and the primary housing half drain.

20. The differential pressure valve of claim 19 wherein the diaphragm is generally circular and of uniform thickness selected from the group consisting of liquid silicone, silicone rubber, or natural rubber.

21. The differential pressure valve of claim 19 wherein said disk is of thickness of about 0.2 to 0.5 mm.

22. The differential pressure valve of claim 19 wherein said secondary housing half further comprises a rubber plug adapted for introducing injected medicine into the fluid flow of the second fluid source.

23. The differential pressure valve of claim 19 wherein said secondary housing half includes threaded means for connecting a fluid source thereto.

* * * * *

UNITED STATES PATENT AND TRADEMARK OFFICE
CERTIFICATE OF CORRECTION

PATENT NO. : 5,935,100
DATED : August 10, 1999
INVENTOR(S) : Jan Willem M. Myers It is certified that error appears in the above-identified patent and that said Letters Patent is hereby corrected as shown below:

<u>Title page,</u>
Item [76], please insert a new item, -- Assignee: Filtertek B.V.  Hebron, Il --.

<u>Column 2,</u>
Line 16, please insert -- *Attorney, Agent, or Firm - Brinks Hofer Gilson & Lione* --.

Signed and Sealed this

Eleventh Day of December, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.     : 5,935,100                                              Page 1 of 1
DATED          : August 10, 1999
INVENTOR(S)    : Myers It is certified that error appears in the above-identified patent and that said Letters Patent is hereby corrected as shown below:

<u>Title page,</u>
Item [56], U.S. PATENT DOCUMENTS" please add
-- 08/781,011    1/1997    Myers --

Signed and Sealed this

First Day of October, 2002

Attest:

Attesting Officer

JAMES E. ROGAN
Director of the United States Patent and Trademark Office